US012712057B2

(12) United States Patent
Breitenstein et al.

(10) Patent No.: US 12,712,057 B2
(45) Date of Patent: Aug. 18, 2026

(54) OPHTHALMIC MICROSCOPE WITH IMPROVED DOCUMENTATION CAPABILITY

(71) Applicant: Haag-Streit AG, Köniz (CH)

(72) Inventors: Jörg Breitenstein, Köniz (CH); Frank Zumkehr, Köniz (CH)

(73) Assignee: Haag-Streit AG, Köniz (CH)

(*) Notice: Subject to any disclaimer, the term of this patent is extended or adjusted under 35 U.S.C. 154(b) by 338 days.

(21) Appl. No.: 18/569,500

(22) PCT Filed: Jul. 5, 2021

(86) PCT No.: PCT/EP2021/068455
§ 371 (c)(1),
(2) Date: Dec. 12, 2023

(87) PCT Pub. No.: WO2023/280371
PCT Pub. Date: Jan. 12, 2023

(65) Prior Publication Data

US 2024/0274250 A1 Aug. 15, 2024

(51) Int. Cl.
*G16H 15/00* (2018.01)
*A61B 3/00* (2006.01)
(Continued)

(52) U.S. Cl.
CPC ........... *G16H 15/00* (2018.01); *A61B 3/0083* (2013.01); *A61B 3/132* (2013.01); *A61B 3/135* (2013.01); *A61B 3/14* (2013.01); *G06F 3/16* (2013.01)

(58) Field of Classification Search
CPC ...... G16H 15/00; A61B 3/0083; A61B 3/132; A61B 3/135; A61B 3/14; G06F 3/16
(Continued)

(56) References Cited

U.S. PATENT DOCUMENTS 6,361,167 B1 * 3/2002 Su .......................... A61B 3/107 351/206
2005/0185138 A1 8/2005 Wong et al.
(Continued)

FOREIGN PATENT DOCUMENTS

CA 3 117 533 4/2020
WO 2013/049854 4/2013
(Continued)

OTHER PUBLICATIONS

Tavazzi et al., "Corneal Pachymetry and Endothelial Microscopy by Slit-Lamp", Novel Diagnostic Methods in Ophthalmology, Internet: https://www.intechopen.com/chapters/66009, pp. 1-14.
(Continued)

*Primary Examiner* — Sharrief I Broome
(74) *Attorney, Agent, or Firm* — GREENBLUM & BERNSTEIN, P.L.C.

(57) ABSTRACT

An ophthalmic microscope assembly has an ophthalmic microscope with a camera, a voice recorder with speech-to-text conversion, a measurement unit for carrying out measurements, and a report generator for generating reports. Depending on the physical input, such as the voice data from the voice recorder, the image data from the camera, the data measured by the measurement unit, as well as the current operating settings of the microscope, report generator automatically generates a report. Depending on the same data, a guide automatically generates guidance to the user and/or performs measurements and takes images. A microphone is placed below the ocular or on the frame of a display of the microscope.

27 Claims, 4 Drawing Sheets

(51) Int. Cl.

| | |
|---|---|
| ***A61B 3/13*** | (2006.01) |
| ***A61B 3/135*** | (2006.01) |
| ***A61B 3/14*** | (2006.01) |
| ***G06F 3/16*** | (2006.01) |

(58) Field of Classification Search
USPC .......................................................... 351/208
See application file for complete search history.

(56) References Cited

U.S. PATENT DOCUMENTS

| | | | | |
|---|---|---|---|---|
| 2012/0069302 | A1* | 3/2012 | Juhasz | A61B 3/117 351/221 |
| 2017/0108685 | A1* | 4/2017 | Casas | G02B 21/086 |
| 2020/0211233 | A1* | 7/2020 | Siegel | G06F 3/013 |
| 2021/0244271 | A1* | 8/2021 | Lee | G02B 27/0149 |
| 2022/0117486 | A1* | 4/2022 | Yoshida | A61B 3/152 |

FOREIGN PATENT DOCUMENTS

| | | | |
|---|---|---|---|
| WO | 2018/026666 | 2/2018 | |
| WO | 2020/180729 | 9/2020 | |
| WO | WO-2020180729 A1 * | 9/2020 | A61B 3/0041 |
| WO | 2021/067624 | 4/2021 | |

OTHER PUBLICATIONS

Wikipedia, “Tear break-up time”, Internet: https://en.wikipedia.org/wiki/Tear_break-up_time, version Jul. 2, 2021.
Int’l Search Report (Form PCT/ISA/210) conducted in Int’l Appln. No. PCT/EP2021/068455 (Mar. 17, 2022).
Int’l Written Opinion (Form PCT/ISA/237) conducted in Int’l Appln. No. PCT/EP2021/068455 (Mar. 17, 2022).

* cited by examiner

90

```
<template>
        <placements>
                <placement>
                        <media>image</media>
                        <category>A4</category>
                        <position>321,20</position>
                        <size>200,140</size>
                </placement>
                <placement>
                        <media>text</media>
                        <category>*</category>
                        <position>0,20</position>
                        <size>300,140</size>
                <placement>
                ...
        </placements>
        ...
</template>
```

OPHTHALMIC MICROSCOPE WITH IMPROVED DOCUMENTATION CAPABILITY

TECHNICAL FIELD

The invention relates to an ophthalmic microscope assembly having a processing unit adapted to generate reports of sessions with the patient.

BACKGROUND ART

Ophthalmic microscopes, i.e. microscopes adapted to examine a patient's eye, record a wealth of parameters. Examples of such microscopes include slit lamp microscopes, fundus microscopes, and OCT microscopes.

Typically, an examination session with a patient includes taking photographs and/or performing other measurements. In addition, the examiner will query the patient and write a report.

Voice recording systems including automated speech-to-text conversion have been known in the medical field to support the examiner in such tasks.

DISCLOSURE OF THE INVENTION

The problem to be solved by the present invention is to provide an ophthalmic microscope assembly and a method for operating it that simplify the generation of medical reports.

This problem is solved by the assembly of claim 1.

Accordingly, the ophthalmic microscope assembly comprises at least the following elements:

A processing unit: This may in particular be a computer, and it may be remote from the microscope or built into the microscope.

An ophthalmic microscope with a camera: This is a microscope adapted to take digital images of a human eye by means of the camera.

A voice recorder: The voice recorder is located within hearing range of the microscope and is adapted to generate voice recordings.

According to the invention, the processing unit is adapted to associate, in a report, voice data from the voice recorder and image data from the microscope.

In this context, "associating" means that it generates a mapping between parts of the voice data and images, which associates each of said parts to one or more individual images. Examples of how to create such a mapping are described below.

The report is a set of data comprising at least the voice data, the image data, and the mapping.

Typically, an ophthalmic microscope has a plurality of operating parameters, such as illumination parameters, the current magnification, the relative horizontal position of the microscope in respect to a patient's headrest, the view angle of the microscope, etc. Advantageously, the microscope is adapted to send operating data indicative of one or more such operating parameters to the processing unit. Further, the processing unit is adapted to automatically associate the operating data with at least one of the voice data and the image data.

This allows to know, from the report, the operating parameters under which certain images and/or voice data were recorded.

In addition or alternatively thereto, processing unit may be adapted to automatically associate, in the report, voice data from the voice recorder and image data from the microscope as a function of the operating data. Hence, the mechanical or electrical settings of the microscope are harnessed, as physical inputs, to automatically and autonomously make reports more meaningful.

Advantageously, the processing unit comprises a speech recognition unit adapted to recognize (at least) keywords and/or key phrases in the voice data. These keywords and/or key phrases, which are physical input, can e.g. be used to automatically categorize the voice data and/or the image data. Hence, the physical recording of speech is harnessed, as a physical input, to automatically make reports more meaningful.

In particular, the processing unit may be adapted to associate, in the report, voice data from the voice recorder and image data from the microscope as a function of the operating data.

The processing unit may also comprise a categorizer in order to attribute the voice data and/image data of a current session, or the current session itself, to a subset of a plurality of predefined categories. Such categories may e.g. be descriptive of at least one of:

what part of the eye is measured which of the eye of a patient is measured, and/or what kind of pathology is being observed, what kind of measurement is being carried out, and/or what is the purpose of the current session.

The "current session" may e.g. be a whole or a part of an examination session with a given patient.

Such a categorizer allows to e.g. attribute images, voice recordings, and/or other datasets and/or a current session to one or more categories.

The processing unit may further comprise:

in its storage, a plurality of stored report templates, and a report generator generating the report as a function of one of the report templates.

This allows to adapt the reports depending e.g. on the category or categories as determined by the categorizer.

The microscope assembly may further comprise a measurement unit adapted to measure at least one eye parameter and generating measurement data indicative of the eye parameter.

In this case, the processing unit may be adapted to associate, in the report, the measurement data with the voice data and/or the image data and/or other datasets. This allows to automatically associate measurement data with a report.

The processing unit may also be adapted to associate, in the report, voice data from the voice recorder and image data from the microscope as a function of the measurement data. Hence, the measured physical values are harnessed, as physical inputs, to automatically make reports more meaningful In particular, the measurement data can be used, by the categorizer, to select the category/categories as a function of the measurement data.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Definitions

The term "ophthalmic microscope assembly" refers to an assembly of a processing unit, a voice recorder, and an ophthalmic microscope. These at least three components may be integrated into a single device or may be formed by two or more separate, connected devices. For example, the processing unit may be a computer separate from the ophthalmic microscope, e.g. a central server computer in a medical facility, connected to the microscope via LAN. The voice recorder may be built into the microscope—or at least its microphone may be built into the microscope—while voice processing software may e.g. be running on the computer mentioned above.

A "value being indicative of a parameter" is to be understood such that the "value" depends on the "parameter" in such a way that the parameter can be retrieved, over at least a plurality of its possible values, from the value. If the parameter is a scalar-valued parameter, the given value is, over at least part of the range of the parameter, advantageously a monotonous function of the parameter. If the parameter has a finite number of possible parameter values, there is advantageously one individual "value" attributed to each parameter value.

Overview

Figure 1:
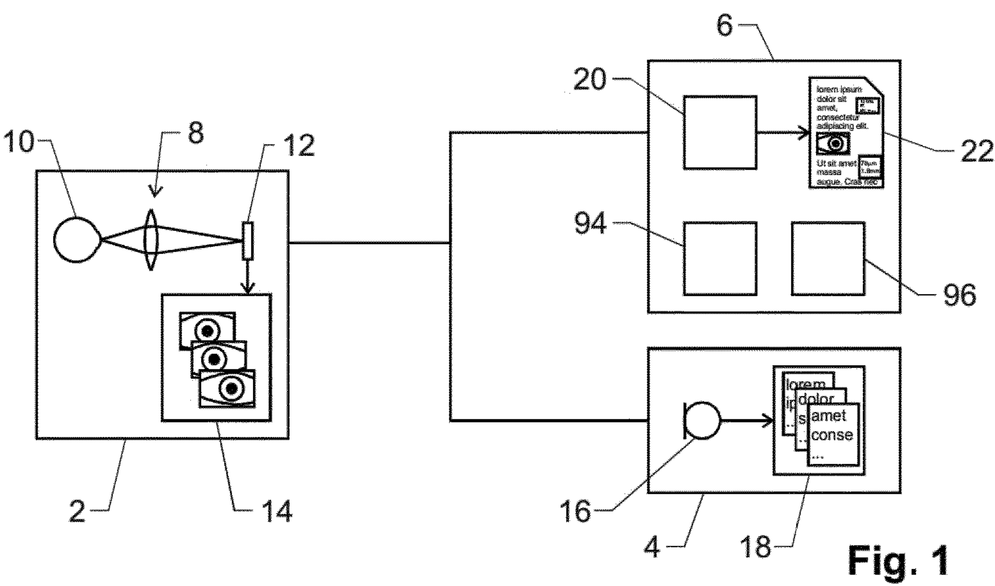
FIG. 1 shows an overview diagram of some of the elements of the ophthalmic microscope assembly.

FIG. 1 shows an ophthalmic microscope assembly having an ophthalmic microscope 2, a voice recorder 4, and a processing unit 6.

Ophthalmic microscope 2 comprises microscope optics 8 for projecting the image of a patient's eye 10 onto a camera 12. It is adapted to generate one or more digital images as image data 14, with the term "images" also encompassing video sequences.

Voice recorder 4 has a microphone 16. It is adapted to generate voice data 18.

Processing unit 6 comprises a report generator 20 adapted to generate, from the image data 14, the voice data 18, and further datasets and category data, as described below, a report 22.

Even though these components have been shown as separate blocks in FIG. 1, it must be noted that they may also share common resources. For example, voice recorder 4 may comprise software that runs on the same computer as report generator 20, and this computer may or may not be integrated in ophthalmic microscope 2.

Ophthalmic Microscope

Figure 2:
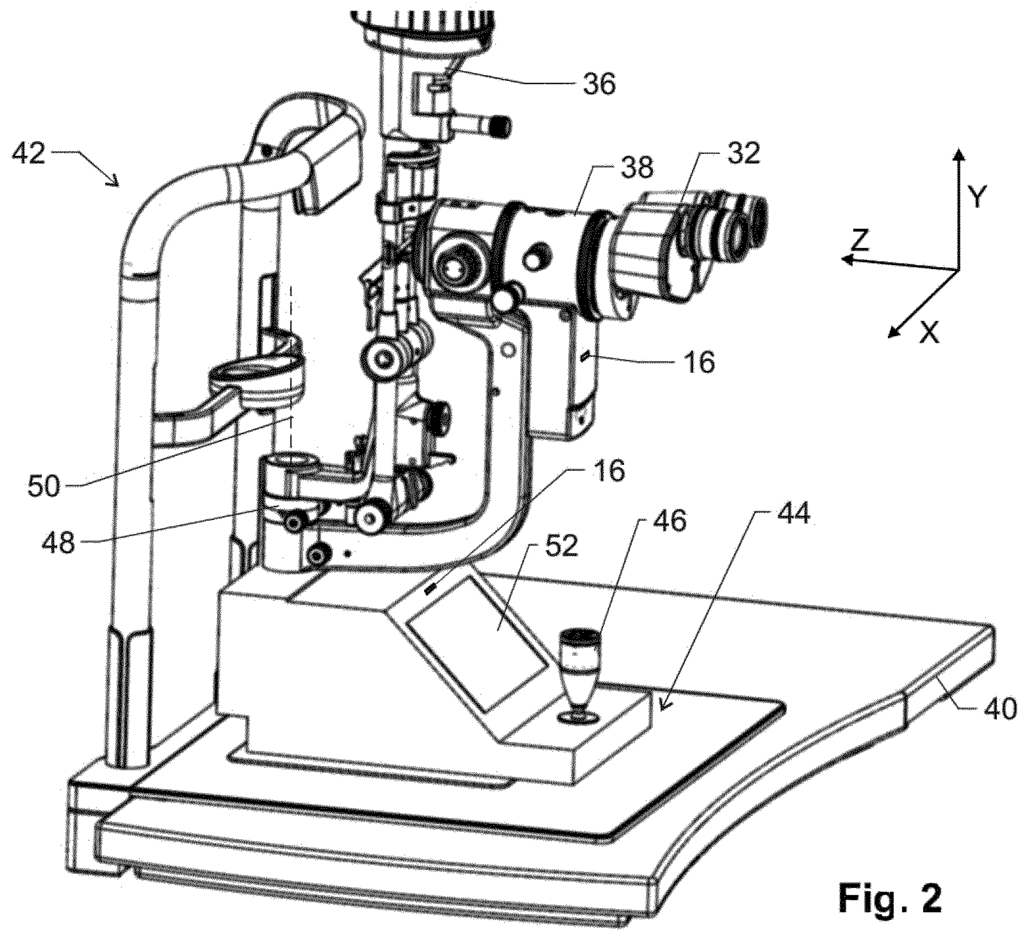
FIG. 2 shows an embodiment of an ophthalmic microscope.
Figures 3, 4, 5:
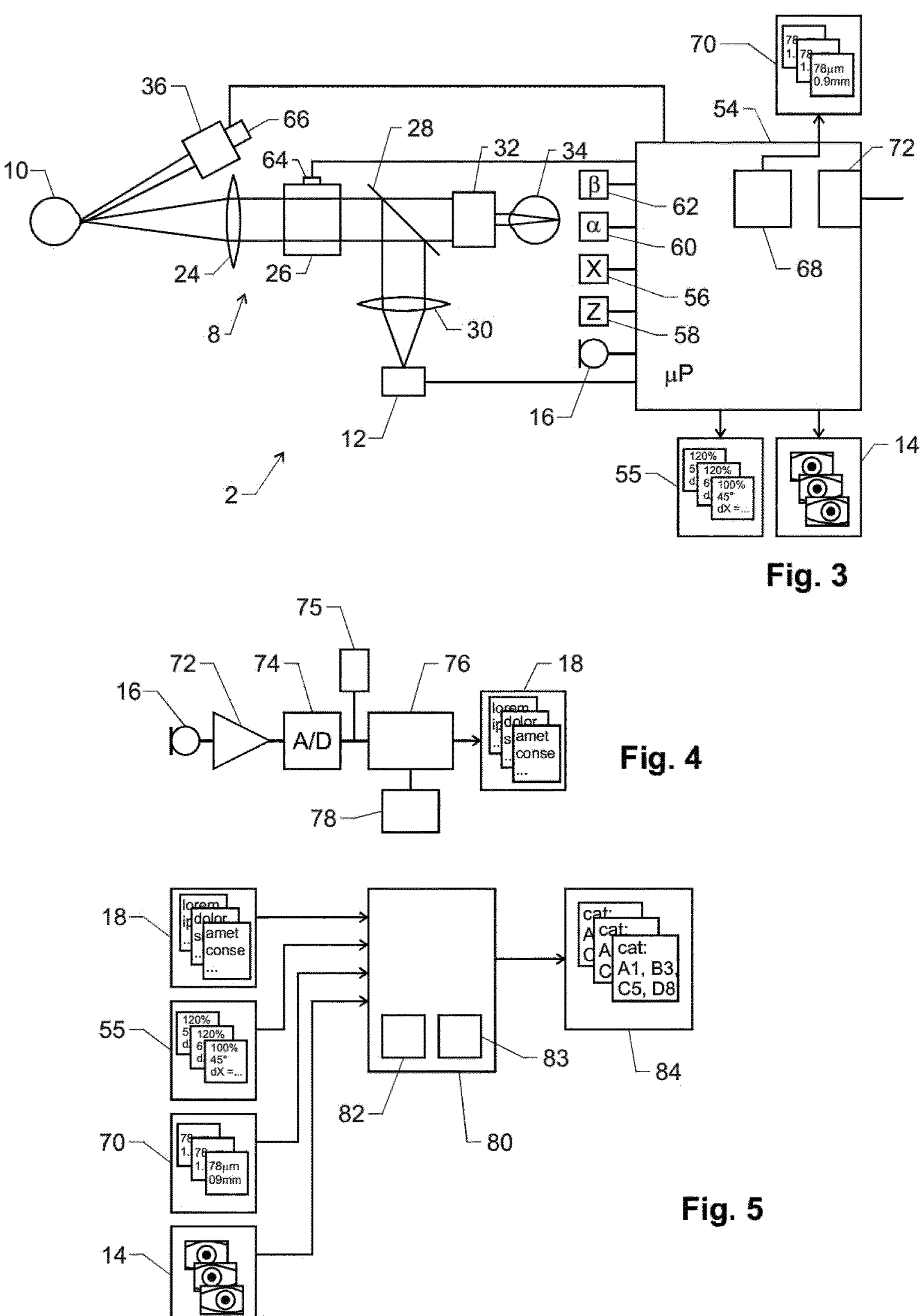
FIG. 3 shows the block diagram of some components of a microscope.
FIG. 4 shows the block diagram of some components of a voice recorder.
FIG. 5 shows the block diagram of some components of a categorizer.

An embodiment of an ophthalmic microscope 2 is shown in FIGS. 2 and 3.

As mentioned, it comprises imaging optics 8 for imaging a patient's eye 10 onto camera 12. For example, and as shown, these optics may comprise an objective lens system 24, an adjustable zoom optics 26, a beam splitter 28, a camera lens system 30, and an ocular 32, with the (optional) ocular 32 projecting the image into a user's eye 34.

Beam splitter 28 splits the light from the patient's eye 10 between camera 12 and ocular 32.

Microscope 2 may further comprise a light source 36 adapted to shine light onto the patient's eye 10.

In the shown embodiment, microscope 2 is a slit lamp microscope, i.e. light source 36 is adapted to cast a slit-shaped field of illumination onto the patient's eye 10. The width of the slit may be adjusted. In addition, other geometries of illumination may be generated as well, and the intensity and/or spectral composition of the light may be varied by the user.

As shown in FIG. 2, imaging optics 8 is arranged in a microscope housing 38. Microscope 2 further comprises a base 40 to be mounted to the surface of a table and forming a stationary frame of reference.

A headrest 42 for supporting the chin of the patient is affixed to base 40.

A stage 44 is mounted to base 40 and is movable in respect thereto (and therefore also in respect to headrest 42 and the patient's eye) along perpendicular horizontal directions X and Z, with Z extending perpendicularly to patient's frontal plane when the patient is installed in headrest 42.

A joystick 46 (or other control means, such as buttons) is provided for the user to displace stage 44 along directions X and Z.

A pivotal connection 48 is mounted to stage 44 and adapted to independently pivot microscope housing 38 and light source 36 in respect to stage 44 about a vertical pivot axis 50. Pivot axis 50 substantially coincides with the apex of the patient's eye when the patient is resting her/his head in headrest 42.

The optical axis of the microscope optics 8 as well as the illumination from illumination source 36 intersect on pivot axis 50.

Microscope 2 may further comprise an (optional) display 52, which may e.g. be mounted to stage 44. In the shown embodiment, microscope housing 38 is pivotally arranged above display 52. Advantageously, display 52 is a touch-screen for receiving user input operating on GUI controls.

One or more microphones 16 facing the user may be arranged on microscope 2. FIG. 2 shows two possible locations for such microphone(s):

- Microphone 16 may be arranged on microscope housing 38 to be close to the user's mouth. This is particularly advantageous if the microscope has an ocular 32 as shown, in which case microphone 16 is best arranged on housing 38 below ocular 32, which is a position close to the user's mouth.
- Microphone 16 may be arranged on the frame of display 52 because the user's mouth will typically also be close to display 52.

As shown in FIG. 3, microscope 2 may further comprise a control unit 54 connected to various components of the device in order to control it, to assess its status, and/or to perform measurements.

In the shown embodiment, control unit 54 is connected to microphone 16 and forms part of voice recorder 4, which will be described in more detail below.

Further, the shown embodiment is equipped with various detectors for detecting its current operating parameters and for generating operating data 55 indicative of the same. The operating parameters may e.g. include one or more of the following:

- An offset dX of stage 44 along direction X in respect to e.g. a central position in front of headrest 42. For this purpose, microscope 2 may comprise an X-detector 56 and be adapted to generate, as operating data, a value of dX, e.g. in mm.
- The position of stage 44 along direction Z in respect to base 40. For this purpose, microscope 2 may comprise a Z-detector 58 and be adapted to generate, as operating data, a value Z that e.g. gives the distance between the foremost part of objective lens system 24 of the microscope and the expected position of the patient's eye 10 when the patient is installed in headrest 42.
- An offset dY of the microscope in respect to the headrest, with dY=0 e.g. denoting the position where the microscope axis is at the center height of the eye to be examined. dY can e.g. by calibrated to 0 at the beginning of a session by aligning the patient's eye with the camera axis.
- The pivotal angle $\alpha$ of the optical axis of microscope 2 in respect to direction Z. For this purpose, microscope 2 may comprise a first goniometer 60 arranged in pivotal connection 48 and generate, as operating data, a value for angle $\alpha$, e.g. in degrees, with zero degrees corresponding to the optical axis being parallel to direction Z.
- The pivotal angle $\beta$ of the illumination axis of illumination source 36 in respect to direction Z. For this purpose, microscope 2 may comprise a second goniometer 62 arranged in pivotal connection 48 and generate, as operating data, a value for angle $\beta$, e.g. in degrees, with zero degrees corresponding to the illumination axis being parallel to direction Z.
- The zoom factor f of zoom optics 26. For this purpose, microscope 2 may comprise a zoom determination unit 64 connected to zoom optics 26 and generating, as operating data, a value for zoom factor f, e.g. in %.
- One or more illumination parameters of illumination source 36. These parameters may include one or more of the following: The brightness pb of illumination source 36; the width pw of the field illuminated by the light source on the patient's eye, i.e. the "slit width" of the slit lamp (and/or one or more other parameters indicative of the geometry of the field); a spectral composition ps of the illumination source 36 if the spectral composition of the light from the illumination source can be varied; etc. For this purpose, microscope 2 may comprise an illumination determination unit 66 connected to illumination source 36.

If any of the above parameters is controlled by control unit 54, the respective detector 56-62 may not be a physical detector but may also be implemented as a software routine adapted to retrieve the current setting from the memory of control unit 54.

Figures 6, 7, 8, 9:
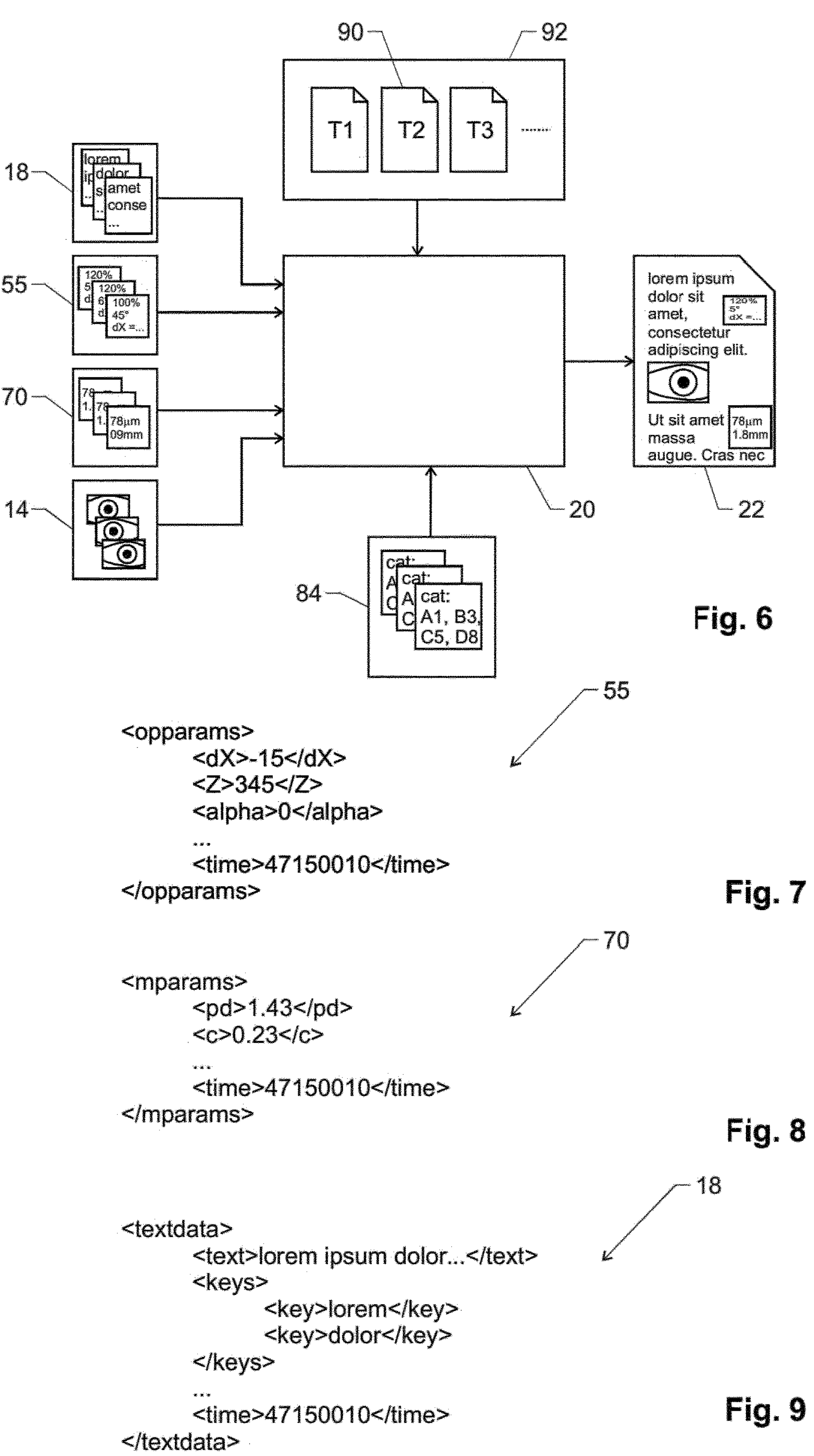
FIG. 6 shows the block diagram of some components of a processing unit.
FIG. 7 shows an example of operating data generated by the microscope.
FIG. 8 shows an example of measurement data generated by the microscope.
FIG. 9 shows an example of speech data generated by the voice recorder.

Control unit 54 is adapted to generate the operating data 55 from these operating parameters. For example, the operating data 55 may be a structured dataset, e.g. a dataset in xml or json format, e.g. such as illustrated in FIG. 7.

As seen, the operating data advantageously also contains a timestamp (<time> . . . </time>) indicative of the time that the given operating data is associated with, e.g. in units of milliseconds since year 2000.

Control unit 54 is advantageously adapted to repetitively generate operating data 55 during a single examination session, e.g. at fixed intervals and/or when the user performs a certain action (e.g. changing settings or taking a picture with camera 12 or initiating a recording of the operating data 55 by voice control).

In addition, and as seen in FIG. 3, control unit 54 is connected to camera 12 for receiving digital images therefrom. These images are stored as image data 14.

Such image data 14 typically comprises, for each image taken, a timestamp indicative of the time the given image was taken. Such a time stamp may e.g. be embedded in the jpeg or mov data of a given image and/or the image data may e.g. comprise an xml or json record with the metadata and a reference to at least one image or video file.

Microscope 2 further comprises a measurement unit 68 adapted to measure at least one eye parameter of the eye 10 being investigated and to generate measurement data 70 indicative of the eye parameter(s).

The Eye Parameters May e.g. Include One or More of the Following:

- Keratometry parameters of the eye: In this case, measurement unit 68 is adapted to perform a keratometry measurement. For example, it may project an illumination image (e.g. a set of concentric circles) onto the eye and to analyze the specular reflection therefrom, e.g. using illumination source 36 and camera 12. The parameters measured may be the curvatures Kh, Kv of the cornea along the horizontal and vertical meridian.
- The cornea thickness ct: In this case, measurement unit 68 is adapted to perform a thickness measurement of the eye, e.g. by illuminating the eye with a thin slit from a defined oblique angle and by processing the image from camera 12, see e.g. Tavazzi et al. in Corneal Pachymetry and Endothelial Microscopy by Slit-Lamp, DOI: http://dx.doi.org/10.5772/intechopen.85037. The parameter may e.g. given in micrometers.
- The pupil diameter pd: In this case, measurement unit 68 is adapted to perform a measurement of pd, e.g. by processing the image from camera 12 and using the current zoom settings to scale it. The parameter measured may e.g. be pd in millimeters.
- The iris diameter id: In this case, measurement unit 68 is adapted to perform a measurement of id, e.g. by processing the image from camera 12 and using the current zoom settings to scale it. The parameter measured may e.g. be id in millimeters.
- A parameter c indicative of the presence of a cataract in the eye: In this case, measurement unit 68 may e.g. be adapted to perform a measurement where the eye is illuminated with a thin slit from a known oblique angle and by processing the image from camera 12, detecting the amount of scattering of the light in the lens of the eye. Alternatively or in addition thereto, measurement unit 68 may be adapted to determine the amount of scattering of light from a frontal overview image of the eye and the gray-level of the pupil. This parameter c may e.g. be a value between 0 and 1, with 0 indicative of no scattering and 1 being indicative of strong scattering.

- Tear break-up time tb (TBUG), in particular as obtained by a NIBUT measurement (Non-Invasive Tear Breakup Time). This time can e.g. be measured by starting a timer when the patient blinks their eye and then measuring the time until specular reflection of the light from the light source starts to degrade, see e.g. https://en.wikipedia.org/w/index.php?title=Tear_break-up_time&oldid=1028519400.

Other Possible Eye Parameters are e.g.:

- reaction speed of pupil diameter to change of illumination,
- Anterior Chamber Depth,
- Dimensions, area, position, and/or opacity of lesions and ulcers,
- Anterior Chamber Angle,
- Graded Corneal Staining, and/or
- Eyelid position.

Control unit 54 is adapted to generate the measurement data 70 from these measured parameters. For example, the measurement data 70 may be a structured dataset, e.g. a dataset in xml or json format, e.g. as illustrated in FIG. 8. Such measurement data again advantageously comprises a timestamp.

Again, control unit 54 may be adapted to generate several sets of measurement data during a single examination session.

Control unit 54 of microscope 2 may further comprise an interface 72 for communicating with processing unit 6. Interface 72 may e.g. a wire-based or wireless LAN interface. The measurement data 70, operation data 55, and image data 14 can be communicated to processing unit 6 by means of interface 72.

Voice Recorder

An embodiment of voice recorder 4 is shown in FIG. 4.

Voice recorder 4 comprises at least one microphone 16, which is located within hearing range of the microscope, i.e. close enough to detect the words of the operator (user) of the microscope. Typically, it will be arranged within 1 meter of less from the microscope.

Advantageously, microphone 16 is arranged on microscope 2 facing the user. Possible locations have been mentioned in the previous section.

The signal of microphone 16 is processed by analog circuitry 72, including an amplifier and/or filter, and converted to digital values by means of an analog-digital-converter 74.

The digitized voice signal may be stored as a voice recording 75, e.g. together with timestamp data for later use.

The digitized voice signal is fed to a speech recognition unit 76, which converts the spoken words into digital text.

Software libraries suitable to implement speech recognition unit 76 are known to the skilled person. Examples include open sourced Common Voice (commonvoice.mozilla.org) or Project DeepSpeech (https://github.com/mozilla/Deep-Speech), or numerous commercial speech recognition libraries, such as the SDK packages provided by Nuance Communications, Inc. (www.nuance.com).

Voice recorder 4 may include natural language parsing capabilities, not only in order to improve speech-to-text accuracy (as implemented in the libraries mentioned above) but also to extract content information.

For example, such language parsing may, in a simple form, comprise keyword and/or key phrase extraction, which can be implemented by comparing the digitized text against a list 78 of keywords and/or key phrases.

The output of voice recorder 4 is the voice data 18. An illustrative example of voice data 18 is shown in FIG. 9. As can be seen, the voice data typically contains the transcribed text. In addition, it may comprise a list of detected keywords and/or key phrases (if the keywords and/or key phrases are detected by voice recorder 4 and not by the categorizer described in the next section). And it advantageously also contains a timestamp.

During an examination session, voice recorder 4 may record one or more such datasets. For example, user input commands (by voice or by operated inputs on e.g. microscope 2) may be used to subdivide session into subsessions encoded in their own datasets, provided with their own keywords and/or key phrases (if applicable), and provided with their own timestamp.

Categorizer

The image data 14, voice data 18, operating data 55, and measurement data 70 (called "datasets" in the following) are now fed to processing unit 6 for generating a report.

Advantageously, processing unit 6 comprises a categorizer 80, see FIG. 5, which is adapted to attribute the datasets and/or the current session to a subset of a plurality of predefined categories.

Categorizer 80 is implemented in software and/or hardware, e.g. in the same computer as the rest of processing unit 6.

Categorization is typically carried out for a "current section", i.e. for a session or subsession taking place during a certain time.

Hence, in a first step, categorizer 80 typically associates different incoming datasets to each other using their timestamps.

For example, categorizer 80 may identify, using the timestamps, which parts of the image data 14, voice data 18, operating data 55, and/or measurement data 70 correspond to the same current session.

Typically, there will be several "classes" of categories, with each class containing several categories. This is best illustrated by a non-limiting example. In this example, there are the following classes of categories:

- Class A: Which part of the eye is being measured (e.g. photographed)? This class may e.g. include the following categories:
  - A1: cornea measurement
  - A2: cross section measurement
  - A3: retina measurement
  - A4: overview image
  - A5: conjunctiva
  - A6: lid
- Class B: Which eye is being measured? This class will typically include the following two categories:
  - B1: left eye
  - B2: right eye
- Class C: What kind of pathology is being observed? This class may e.g. include categories such as
  - C1: glaucoma
  - C2: cataract
  - C3: cornea abrasion
- Class D: What kind of measurement is being carried out, i.e. what is the technical nature of the investigation? This class may e.g. include categories such as:
  - D1: measurement with narrow-slit illumination, i.e. where the light field has a width on the patient's eye of less than a given threshold, e.g. of less than 0.5 mm.

D2: measurement with wide-field illumination, i.e. where the light field has a width on the patient's eye of more than a given threshold, e.g. more than 3 mm.

D3: fluorescence measurements, i.e. a measurement where fluorescence from the eye is detected using illumination of a specific spectral composition and/or one or more filters between the patient's eye 10 and camera 12.

Class E: What is the purpose of the current session? This class may e.g. include categories such as:

E1: General examination

E2: Tear film examination

E3: Anterior chamber examination

E4: Fundus examination

Other categories in this class and/or in class A may e.g. include, in addition to or alternatively to the above at least one of "conjunctiva diffuse", "conjunctiva narrow slit", "cornea narrow slit", "cornea retro", "cornea tangential", "cornea moderate slit", "cornea fluorescein", "iris tangential", "lens moderate slit", "lens narrow slit", "lens retro", "lid ir", "overview diffuse".

The datasets or the current session are now automatically attributed to subsets of these categories. For each dataset, one or more classes can be defined, and from each class, one category is selected.

A primary purpose of this process is to attribute the voice data and the image data to specific categories. The information in the datasets is used for this categorization.

Some particularly important examples how to automatically determine categories based on the datasets (and therefore the physical parameters provided to categorizer 80) are given in the following.

Categories Using Operating Data:

In particular, categorizer 80 may be adapted to select the subset of categories as a function of the operating data 55 from microscope 2. For example, the operating data can be used as follows for categorization:

If the value of dX is >0, then it can be assumed that the user has adjusted the microscope to view the patient's right eye (category B2 of class B). Otherwise, the category in class B would be B1. Hence, in this embodiment, the categories are at least indicative of which eye is being measured and categorizer 80 is adapted to determine, as a function of the X-offset dx, if the left eye or the right eye of the patient is being measured.

If the value of Z (i.e. basically the distance between microscope objective 24 and headrest 42) is above a given threshold, it can be assumed that the user has inserted dedicated fundus optics between the microscope optics and the patient. In that case, the category in class A may be determined to be a "retina measurement" (category A3).

On the other hand, if the value of Z is below this given threshold and, in addition, the pivotal angle β of illumination source 36 is within a given range (e.g. >25°) and the width pw of the illuminated field on the eye is below a threshold (e.g. <0.2 mm), it can be assumed that the user is recording a cross section of the anterior chamber and the lens (category A2 of class A).

If the width pw of the illuminated field is large (e.g. >2 cm) it can be concluded that the categories A4, A5, or A6 of class A might apply (this can be combined with the result from the image classifier, see below, to determine which of the categories may apply).

Categories Using Voice Data:

Categorizer 80 may also be adapted to select the subset of categories as a function of the recognized keywords and/or key phrases in the voice data. Key phrases may e.g. comprise a sequence of keywords and/or information derived from syntactically parsed sentences. Examples:

If keywords such as "fundus" or "retina" are present in the voice data, and in particular of they have a high occurrence, it can be assumed that the user is running a retina measurement (category A3 of class A). This may be combined with the value of Z for higher accuracy of the categorization, see above.

If the keyword "glaucoma" is present in the voice data, it can be assumed that the user is assessing glaucoma pathology (category C1 of class C). Similarly, the keywords "cataract" or "cornea abrasion" may be used for categorization into categories C2 and C3, respectively.

If the key phrase "left eye" is used and in particular of it has a high occurrence, it can be assumed that the user is investigating the left eye of the patient (category B1 of class B). This may be corroborated with the value dX.

If the key phrase "general examination" is used, it can be assumed that the current session is an overview session (category E1 of class E).

Categories Using Image Data:

Categorizer 80 may comprise an image classifier 82 attributing the images from image data 14 to one (or a subset) of several image classes. In this case, the categorizer is adapted to select the subset of categories as a function of the attributed image classes.

Suitable image classifiers may e.g. be based on neural networks, such as implemented in the TensorFlow library (www.tensorflow.org).

The classifier is trained on a set of typical images recorded by the camera during certain categories of sessions.

Figures 10, 11:
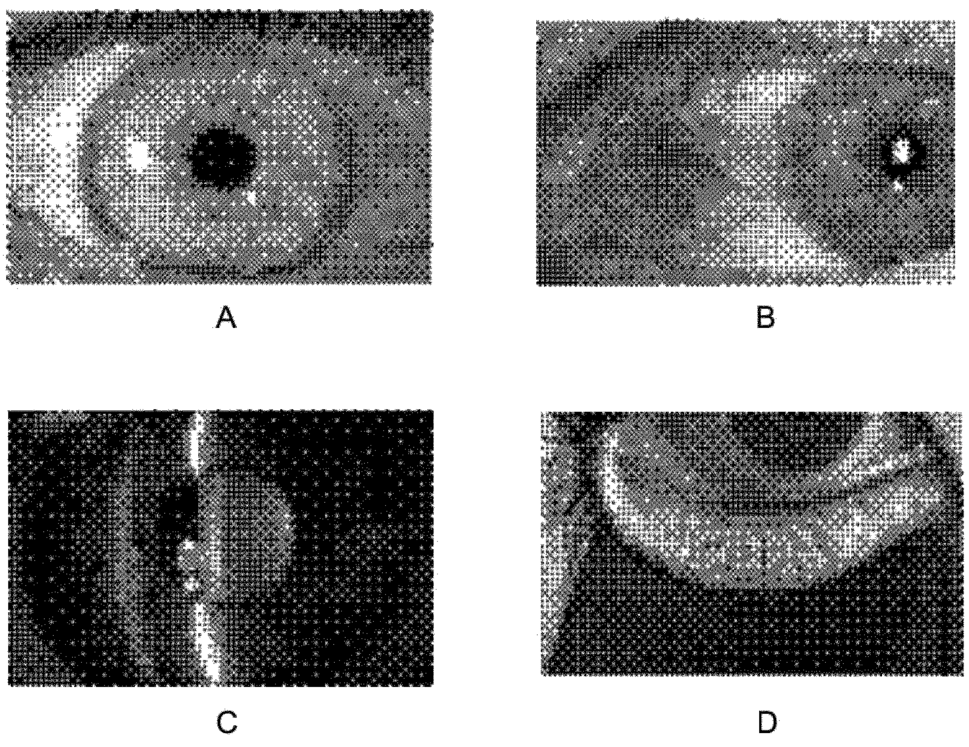
FIG. 10 shows some types of images used for training an image classifier (black-and-white dithered for printing—in reality, grayscale or color images are advantageously used)
FIG. 11 shows an example of data in a template.

FIG. 10 shows some types of images that can be used for training the classifier. For example:

To train image classifier 82 to recognize "overview images" showing the whole eye in diffuse illumination: Record a plurality of such images, as the one shown in FIG. 10A, from different patients in different sessions, and use them in the training dataset for the category "overview" (category A4 above).

To train image classifier 82 to recognize "conjunctiva images" showing shots of the conjunctive in diffuse illumination: Record a plurality of such images, as the one shown in FIG. 10B, for varying parts of the conjunctiva from different patients in different sessions, and use them in the training dataset for the category "conjunctiva" (category A5 above).

To train image classifier 82 to recognize narrow slight measurements of the anterior chamber and lens: Record a plurality of such images, as the one shown in FIG. 10C, from different patients in difference sessions, arranging the illumination source under varying angles, and use them in the training dataset for the category "cross section measurement" (category A2 above).

To train image classifier 82 to recognize lid photographs: Record a plurality of such images, such as the one shown in FIG. 10D, from different patients in difference sessions and of different parts of the lids, and use them in the training dataset for the category "lid" (category A6 above).

After such a training, classifier 82 will be able to attribute the images from image data 14 to one of several image types (i.e. categories of class A in the example above), which in turn allows classifier 80 to select the subset of categories as a function of the attributed image types.

Advantageously, when using TensorFlow for image classification, the log its derived from the model may be converted to probabilities using a softmax layer. In a simple approach, the highest probability class can then be used as the one identifying the category of a given image.

Categories Using Measurement Data:

Categorizer 80 may also be adapted to select the subset of categories as a function of the measurement data 70. Examples:

- If measurement data 70 includes the cornea thickness ct of the eye, the category in class A can be assumed to be A2 ("cross section measurement") if the microscope is a slit lamp microscope.
- If parameter c is indicative of the presence of a cataract, it can be assumed that the category in class C may be C2 ("cataract").

Categories Using Manual Input:

Categorizer 80 may further comprise a category selector 83 adapted to receive manual input, from the user, where the user can attribute one or more categories to a dataset and/or the current session.

Category selector 83 may e.g. be implemented the hard- and software of microscope 2. It comprises user input elements, which may e.g. be embodied by user interface elements brought up on touchscreen display 52 to be operated by the user.

In particular, the user may use category selector 83 for specifying the type of the current session (class E) and/or the user may categorize individual photographs (class A).

Combining Categories:

Categorizer 80 is typically adapted to combine the categories derived from the operating data, voice data, image data and/or measurement data. Such a combination may be implemented in different ways:

- Some categories may be determined from only one dataset. For example, the category in class B may be determined from the operating data 55 alone, in particular from offset dX. This category may be combined with categories in other classes.
- Other categories may be derived from different sources. For example, the image data 14 as well as the operating data 55 may indicate a category in class A. If both datasets indicate the same category, then this category can be assumed to apply to the current session. If contradictive results are obtained, the respective categories may not be attributable to the current session. In that case, an error may be raised (e.g. by the "report generator" as described below) or the respective categories may only be attributed to the image data and operating data, but not to the current session as a whole.

The output of categorizer 80 is categorization data 84. Such data can be assigned to the current session as a whole, or to individual records in image data 14, voice data 18, operating data 55, and/or measurement data 70.

For Example:

- The category derived by image classifier can be attributed to the classified image. In addition, it may also be attributed to the current session.
- The category or categories derived from voice data having a certain timestamp is/are attributed to the respective record of the voice data but also to a record of the image data if there is image data having the same timestamp.

Hence, the category data 84 may comprise categories attributed to records of the image data, voice data, operating data, and/or measurement data, but it may also comprise categories attributed to the current session.

Report Generator

The category data 84 as well as the other datasets 14, 18, 55, 70 (the latter optionally with categories attributed to them) are provided to report generator 20, which then generates a report 22 therefrom. An embodiment of report generator 20 is shown in FIG. 6.

Report generator 20 is implemented as hardware and/or software in processing unit 6.

A report is a structured document (i.e. a file or a collection of files or a collection of database records), advantageously comprising at least:

- Text sections derived from the text data 18,
- Images (including videos) derived from the image data 14,
- Association data associating at least some text sections and some images from the text data 18 and image data 14.

In Addition, the Report May Comprise:

- Measurement results derived from the measurement data 70. In this case the relational data is also indicative of relations between the text sections and/or images and the measurement results and/or the measurement results are encoded in the text sections and/or the images.
- Operating information derived from the operating data 55. In this case the relational data is also indicative of relations between the text sections and/or images and the operating information and/or the operating information is encoded in the text sections and/or the images.

Report 22 May Come in Various Forms:

- Report 22 may be a formatted document comprising location information for the text sections and images (and, where applicable, measurement results and/or operating information) to be displayed. Such a formatted document can e.g. be encoded as a pdf document, an html document, or any other document type comprising information for laying out at least text sections and images. This type of document is primarily used for being displayed on screen or for being printed. In this case, the "association data" e.g. includes the relative positions or absolute positions of parts of the text sections and at least some of the images. The elements being next to each other in the report are associated with each other, i.e. the "association" is, in this embodiment, implemented by means of the location information, with elements having locations next to each other being associated to each other.
- Report 22 may be a relational document not necessarily comprising location information. Rather, it may merely encode what images are associated with which text sections or (and, where applicable, which measurement results and/or operating information are associated with which text sections and/or images). Such a document may e.g. a collection of xml or json records with cross references and image data and/or it may be a set of records in a sql database. In this embodiment, the association is implemented by the xml/json/sql records having index entries pointing to other records or to image files. For example, an xml record identifying a text section may have at least one <image> entry identifying the unique ID or file path of an image and vice versa.

Report 22 may also include the "raw data", in particular the original digitized voice recording 75 as recorded by voice recorder 4.

In particular if report 22 is a formatted document, report generator 20 may be provided with report templates 90 stored in memory 92 of processing unit 6. Report generator 20 is adapted to generate the report 22 as a function of one of the report templates 90.

In particular, report generator 20 is advantageously adapted to select one of the report templates 90 by using at least one of the following methods A and B:

A) Report generator 20 provides a user-operatable selection mechanism, e.g. on the touchscreen display of microscope, where the user can select a template.

B) Report generator 20 is adapted to automatically:
  select one template and/or
  suggest one or more templates, e.g. on display 52, for selection by the user, based on the category data 84, in particular based on the category data attributed to the current session. For example, each template 80 may comprise data identifying one of the categories of class E, which is then compared to the category data 84 for the current session.

Report generator 20 can implement method A, method B, or both methods.

Advantageously, each report template 90 comprises at least placement instructions, with each placement instruction e.g. comprising:

A media type (e.g. "text" or "image")

Category information (e.g. a category of class A above)

Position information (e.g. the absolute coordinates and size on a page).

A simple example of such a template is shown in FIG. 11. It comprises a first placement instruction for an image with category A4 ("overview"). If report generator 20 finds an image of this category in image data 14, it will place it at the given position (321, 20) of the report and scale it to the given size (200, 140).

The template contains a second placement instruction for text, and (in the example of FIG. 11) the category information is given as "*", which may be interpreted as "any category". Hence, report generator 20 will e.g. look for the first text record for the current session found in text data 14, and render it at the given position (0, 20) with the given size (300, 140).

This will, for example, result in a report having an overview image on the right side and a transcription of the user's text recording on the left.

The templates 90 may also include placement information for at least one of the following:

Placing operating data, e.g. for placing the zoom factor f into a text box below the overview image.

Placing the measured cornea thickness ct into a textbox next to an image of category A2 (cross section measurement).

Placing categories into a text box listing the categories of a text record next to the text section showing the text of this text record.

Guide

As shown in FIG. 1, processing unit 6 (or another part of the microscope assembly, such as the microcontroller of microscope 2) may further comprise a guide 94.

Guide 94 may be implemented in the hardware or software of processing unit 6.

It is adapted to test, using the category or categories attributed to the current session, if the current session is a "guided session".

To do so, processing unit 6 comprises, in its memory, a list 96 of guided categories and, for each guided category, a list of required measurements to be taken. In this context, "measurements" includes measurements to be carried out by measurement unit 68 as well as photographs to be taken by camera 12.

So, for example, list 96 may indicate that category E1 ("general examination") is a guided category, and it indicates that an overview image has to be taken if the current session is a "general examination" and that the cataract parameter c as mentioned above has to be measured.

Hence, when the current session is in category E1, guide 94 will display, in display 52, that an overview image has to be taken and the cataract parameter c has to be measured. In addition or alternatively thereto, guide 94 will automatically trigger microscope 2 to take an overview image and/or to measure the cataract parameter c.

If microscope 2 is fully automated, guide 94 may set the operating parameters of microscope 2 such that the overview image can be taken and the cataract parameter can be calculated therefrom, and it will trigger the recording of the photograph and the measurement of the cataract parameter. Alternatively, it may wait until the user has e.g. set the position of microscope 2 and illumination source 36 to be suitable for such an image, at which time guide 94 may automatically trigger the taking of the overview image. Alternatively, the user may trigger the taking of the overview image.

Once that categorizer 80 has categorized an image as an overview image, guide 94 will mark the required overview image to be taken.

Hence, in more general terms, the invention also relates to a microscope assembly where at least some of the categories are guided categories, the processing unit comprises a stored list 96 storing, for each guided category, a list of required measurements, and the microscope assembly comprises a guide 94 adapted to test if the current session is categorized as a guided category and, if yes to automatically display guidance listing the required measurements on a display 52 and/or to automatically execute at least part of the required measurements.

And, in particular, the stored list 96 comprises for at least some of the guided categories, a list of required images. In this case, if the current session is categorized as a guided category, guide 94 is adapted to check if the categorized guided category comprises a list of required images and if yes:

to display, on the display 52, instructions indicative of the list of required images and/or to compare the categories of recorded images in the image data 14 against the list of required images.

Notes

In the above examples, timestamps have been attributed to various datasets. If a given dataset is pertinent not only to a moment in time (such as a single image) but to a period in time (such as a video sequence in the image data or a sequence of speech in the voice data), a duration may be attributed to the respective record in the dataset in addition to a time stamp. The duration may e.g. be encoded by the duration per se or by an end time pertinent to the record in the dataset.

In the above embodiment, a manual category selector 83 and/or a manual user selection for templates may be provided. Alternatively, though, the system can be designed to generate the reports without user intervention.

The microscope assembly may also be connected to other instruments and/or a database of medical records from where the report generator may retrieve further information, e.g. for a given patient, to be added to the report.

While there are shown and described presently preferred embodiments of the invention, it is to be distinctly understood that the invention is not limited thereto but may be otherwise variously embodied and practiced within the scope of the following claims.

The invention claimed is:

1. An ophthalmic microscope assembly comprising:

a processing unit, an ophthalmic microscope with a camera, and a voice recorder, wherein the microscope sends operating data indicative of one or more operating parameters of the microscope to the processing unit, and wherein the processing unit associates, in the report, voice data from the voice recorder and image data from the microscope as a function of the operating data by generating a mapping between parts of the voice data and images.

2. The ophthalmic microscope assembly of claim 1, wherein the ophthalmic microscope comprises:

a patient's headrest;

a microscope housing including microscope optics and the camera;

a translational stage between the headrest and the microscope housing;

wherein the translational stage is adapted to displace the microscope housing with respect to the headrest along a horizontal direction Z defining a distance between the headrest and the microscope housing, and a horizontal direction X perpendicular to direction Z; and a pivotal connection mounted to the translational stage, wherein the pivotal connection is rotates the microscope housing with respect to the translational stage about a vertical pivot axis;

wherein the operating data is indicative of at least one of:

an X-offset along the horizontal direction X, or a pivot angle about the pivot axis.

3. The ophthalmic microscope assembly of claim 1, wherein the ophthalmic microscope comprises an illumination source projecting light onto a patient's eye, wherein the operating data is indicative of at least one illumination parameter of the illumination source.

4. The ophthalmic microscope assembly of claim 3, wherein the illumination parameter is at least one of:

a brightness of the illumination source, a width of a field illuminated by the illumination source on a patient's eye, a spectral composition of light generated by the illumination source, or a pivotal angle of the light source.

5. The ophthalmic microscope assembly of claim 1, wherein the processing unit comprises a speech recognition unit that recognizes keywords and/or key phrases in the voice data.

6. The ophthalmic microscope assembly of claim 1, wherein said processing unit comprises a categorizer attributing the voice data and/or the image data of a current session and/or the current session itself to a subset of a plurality of predefined categories.

7. The ophthalmic microscope assembly of claim 1, wherein the ophthalmic microscope sends operating data indicative of one or more operating parameters of the microscope to the processing unit, and the processing unit associates the operating data with at least one of the voice data and the image data and/or associates, in the report, voice data from the voice recorder and image data from the microscope as a function of the operating data, and wherein the categorizer selects the subset of categories as a function of the operating data.

8. The ophthalmic microscope assembly of claim 7, wherein the ophthalmic microscope comprises:

a patient's headrest;

a microscope housing including microscope optics and the camera;

a translational stage between the headrest and the microscope housing, wherein the translational stage displaces the microscope housing with respect to the headrest along a horizontal direction Z defining a distance between the headrest and the microscope housing, and a horizontal direction X perpendicular to direction Z, and a pivotal connection mounted to the translational stage, wherein the pivotal connection rotates the microscope housing with respect to the translational stage about a vertical pivot axis;

wherein the operating data is indicative of at least one of:

an X-offset along the horizontal direction X or a pivot angle about the pivot axis, and wherein the categories are at least indicative of which eye is being measured, and the categorizer determines, as a function of the X-offset, if a left eye or a right eye is being measured.

9. The ophthalmic microscope assembly of claim 6, wherein the processing unit comprises a speech recognition unit recognizing at least one of keywords and key phrases in the voice data, and wherein the categorizer selects the subset of categories as a function of the recognized keywords and/or key phrases.

10. The ophthalmic microscope assembly of claim 6, wherein the categorizer comprises an image classifier attributing images from the image data to one of several image types, and wherein the categorizer selects the subset of categories as a function of the attributed image types.

11. An ophthalmic microscope assembly comprising:

a processing unit;

an ophthalmic microscope with a camera; and a voice recorder;

wherein the processing unit associates, in a report, voice data from the voice recorder and image data from the ophthalmic microscope by generating a mapping between parts of the voice data and images, wherein said processing unit comprises a categorizer attributing a current session to a subset of a plurality of predefined categories, wherein at least some of the categories are guided categories, and wherein the processing unit comprises a list storing, for each guided category, a list of required measurements, and the ophthalmic microscope assembly comprises a guide that tests if the current session is categorized as a guided category and, if yes displays guidance on a display and/or automatically executes at least part of the required measurements.

12. The ophthalmic microscope assembly of claim 11, wherein the stored list comprises for at least some of the guided categories, a list of required images, if the current session is categorized as a guided category by the guide, the guide checks if the categorized guided category comprises a list of required images and if yes:

displays, on the display, instructions indicative of the list of required images and/or compares the categories of recorded images in the image data against the list of required images.

13. The ophthalmic microscope assembly of claim 1, wherein the processing unit comprises:

a storage storing a plurality of report templates, and a report generator generating the report as a function of one of the report templates.

14. The ophthalmic microscope assembly of claim 13, wherein the report templates comprise placement instructions indicative of a position of a text sequence of the voice data and/or an image of the image data in the report, wherein the placement information comprises category information, and the report generator uses the placement information for placing a given voice sequence or image in the report depending on a category attributed to the given voice sequence or image mages and on the category information.

15. An ophthalmic microscope assembly comprising:

a processing unit;

an ophthalmic microscope with a camera, and a voice recorder;

wherein the processing unit associates, in a report, voice data from the voice recorder and image data from the microscope by generating a mapping between parts of the voice data and images, wherein said processing unit comprises a categorizer attributing the voice data and/or the image data of a current session and/or the current session itself to a subset of a plurality of predefined categories, wherein the processing unit comprises a storage storing a plurality of report templates, and a report generator generating the report as a function of a first template of the report templates, wherein, based on the subset, the report generator selects the template and/or displays one or more templates for selection of the first template by the user.

16. The ophthalmic microscope assembly of claim 6, wherein the categorizer further comprises a category selector receiving manual input for attributing one or more categories to a dataset and/or to a current session.

17. The ophthalmic microscope assembly of claim 1, further comprising a measurement unit measuring at least one eye parameter of an eye being investigated and generating measurement data indicative of the eye parameter, wherein the processing unit associates, in the report, the measurement data with the voice data and/or the image data and/or wherein the processing unit associates, in the report, voice data from the voice recorder and image data from the microscope as a function of the measurement data.

18. The ophthalmic microscope assembly of claim 17, wherein said processing unit comprises a categorizer attributing the voice data and/or the image data of a current session and/or the current session itself to a subset of a plurality of predefined categories and wherein the categorizer selects the subset of categories as a function of the measurement data.

19. The ophthalmic microscope assembly of any of claim 17, wherein the eye parameter comprises at least one of keratometry data of the eye, a cornea thickness of the eye, a parameter indicative of a presence of a cataract in the eye, a pupil diameter of the eye, and/or an iris diameter of the eye, tear break-up time of the eye, anterior chamber depth, dimension and opacity of lesions and ulcers, anterior chamber angle, graded corneal staining, eyelid position.

20. The ophthalmic microscope assembly of claim 1, wherein the voice recorder comprises at least one microphone and wherein the microphone is arranged on the ophthalmic microscope.

21. The ophthalmic microscope assembly of claim 20, wherein the ophthalmic microscope comprises a pivotal microscope housing, and wherein the microphone is arranged on the pivotal microscope housing.

22. The ophthalmic microscope assembly of claim 21, wherein the microscope comprises an ocular on the microscope housing, and the microphone is arranged below the ocular.

23. The ophthalmic microscope assembly of claim 21, wherein the ophthalmic microscope comprises a display, with the pivotal microscope housing being pivotal in respect to the display, and wherein the microphone is arranged on a frame of the display (52).

24. An ophthalmic microscope assembly comprising:

a processing unit;

an ophthalmic microscope with a camera; and a voice recorder;

wherein the processing unit associates, in a report, voice data from the voice recorder and image data from the microscope by generating a mapping between parts of the voice data and images, wherein the microscope sends operating data indicative of one or more operating parameters of the microscope to the processing unit, and wherein the processing unit associates the operating data with at least one of the voice data and the image data and/or associates, in the report, voice data from the voice recorder and image data from the microscope as a function of the operating data, wherein the ophthalmic microscope comprises:

a patient's headrest;

a microscope housing including microscope optics and the camera;

a translational stage between the headrest and the microscope housing, wherein the translational stage is adapted to displace the microscope housing with respect to the headrest along a horizontal direction Z defining a distance between the headrest and the ophthalmic microscope housing, by an X-offset along a horizontal direction X perpendicular to direction Z, and a pivotal connection mounted to the translational stage, wherein the pivotal connection provides for a rotation of the microscope housing with respect to the translational stage by a pivot angle about a vertical pivot axis, wherein the operating data is indicative of at least one of:

the X-offset along the horizontal direction X, or the pivot angle about the pivot axis, and wherein the ophthalmic microscope assembly comprises at least one of:

a detector detecting the X-offset, a detector detecting the pivot angle.

25. The ophthalmic microscope assembly of claim 5, wherein the processing unit associates, in the report, voice data from the voice recorder and image data from the microscope as a function of the keywords and/or key phrases.

26. The ophthalmic microscope assembly of claim 6, wherein the categories are indicative of at least one of the following:

a part of an eye is being measured, which eye is being measured, what kind of pathology is being observed, what kind of measurement is being carried out, or what is the purpose of a current session.

27. The microscope ophthalmic assembly of claim 13, wherein the report generator selects the one of the report templates as a function of category data attributed to the current session and/or selects the one of the report templates as a function of user input.

* * * * *